United States Patent [19]

Simpson et al.

[11] Patent Number: 6,051,239

[45] Date of Patent: Apr. 18, 2000

[54] COMPOSITIONS AND METHODS FOR SYSTEMIC DELIVERY OF ORAL VACCINES AND THERAPEUTIC AGENTS

[75] Inventors: Lance Simpson, Moorestown; Nikita Kiyatkin, Cherry Hill, both of N.J.; Andrew Maksymowych, Gulph Mills, Pa.

[73] Assignee: Thomas Jefferson University, Philadelphia, Pa.

[21] Appl. No.: 08/954,302

[22] Filed: Oct. 20, 1997

[51] Int. Cl.[7] .......................... A61K 39/08; C07K 14/33; C07K 19/00

[52] U.S. Cl. ................... 424/239.1; 424/832; 424/190.1; 424/192.1; 530/350; 435/69.3; 435/69.7

[58] Field of Search ............................. 424/184.1, 192.1, 424/247.11, 183.1, 94.1, 239.1, 832, 190.1, 94.63; 530/350; 435/183, 212, 69.3, 69.7

[56] References Cited

U.S. PATENT DOCUMENTS 5,919,665   7/1999   Williams ................................. 435/71.1

FOREIGN PATENT DOCUMENTS

WO 96/12802   5/1996   WIPO.
WO96/40229   12/1996   WIPO.

OTHER PUBLICATIONS

Zhou, et al. 1995 Biochemistry, vol. 34 p. 15175.

Clayton et al., "Protective Vaccination with a Recominbinant Fragment of *Colstridium botulinum* Neurotoxin Serotype A Expressed from a Synthetic Gene in *Escherichia coli*," Infection and Immunity 1995 63(7):2738–2742.

Kimura et al., "The Complete Nucleotide Sequence of the Gene Coding for Botulinum Type C1 Toxin in the C–ST Phage Genome," Biochem. Biophys. Res. Comm. 1990 171:1304–1311.

Laemmli U.K., "Cleavage of Structural Proteins during the Assembly of the Head of Bacteriophage T4," Nature 1970 22:680–685.

LaPenotiere et al., "Expression of a Large, Nontoxic Fragment of Botulinum Neurotoxin Serotype A and its Use as an Immuniogen," Toxicon 1995 33(10):1383–1386.

Lautenslager, G.T. and Simpson, L.L., "Chimeric Molecules Constructed with Endogenous Substances," Advances in Molecular and Cell Biology, vol. 9, pp. 233–262, JAI Press, Inc. (1994).

Montecucco, C. and Schiavo, G., "Mechanism of Action Tenanus and Botulinum Neurotoxins," Mol. Microbiol. 1994 13:1–8.

Neimann et al., Clostridial Neurotoxins: From Toxins to Therapeutic Tools?, Behring Inst. Mitt. 1991 89:153–162.

Rosahl et al., "Short–Term Synaptic Plasticity is Altered in Mice Lacking Synapsin I," Cell 1993 75:661–670.

Sambrook et al., 1989 Molecular Cloning: A Laboratory Manual, 2nd ed., Cold Spring Harbor Laboratory Press, Cold Spring Harbor, NY.

Simpson L.L., "Molecular Pharmacology of Botulinum Toxin and Tetanus Toxin," Annu. Rev. Pharmacol. Toxicol. 1986 26:427–453.

Simpson et al., "Isolation and Characterization of a Novel Human Monoclonal Antibody that Neutralizes Tetanus Toxin," J. Pharmacol. Exp. Ther. 1990 254:98–103.

Primary Examiner—Mary E. Mosher
Attorney, Agent, or Firm—Seidel Gonda Lavorgna & Monaco, PC

[57] ABSTRACT

Compositions and methods of oral delivery of an antigen or therapeutic agent to the general circulation using a modified botulinum toxin which is capable of translocating from the gut to the general circulation but which is altered to be nontoxic are provided.

2 Claims, 1 Drawing Sheet

COMPOSITIONS AND METHODS FOR SYSTEMIC DELIVERY OF ORAL VACCINES AND THERAPEUTIC AGENTS

INTRODUCTION

This invention was made in the course of research sponsored by the National Institutes of Health. The U.S. Government may have certain rights in this invention.

FIELD OF THE INVENTION

The present invention relates to compositions and methods for systemic delivery of orally administered vaccines and therapeutic agents via a modified botulinum toxin, wherein said toxin maintains its ability to translocate across the gut wall but has been altered to be non-toxic.

BACKGROUND OF THE INVENTION

Clostridial neurotoxins are the most potent protein toxins known. The neurotoxin produced from *Clostridium tetani* (tetanus toxin) is encountered by humans as a result of open wounds. However, tetanus poisoning at least in industrial countries is no longer a major public health problem due to the availability and widespread use of a safe, effective and inexpensive vaccine. This vaccine is basically a formalin-inactivated culture supernatant from *C. tetani* grown in fermentors.

*Botulinum neurotoxin* (BoNT), which is produced by the organisms *Clostridium botulinum, Clostridium butyricum* and *Clostridium baratii*, is the potent etiologic agent associated with the disease botulism (Simpson, L. *Annu. Rev. Pharmacol. Toxicol.* 1986 26:427–453). Humans are usually exposed to this neurotoxin through food poisoning, although there are rare incidents of wound botulism. A similar vaccine to the tetanus vaccine has been developed to provide protection from botulinum toxin poisoning. However, since there are seven different serotypes of botulinum toxin, complete protection with this inactivated toxin can be afforded only by making seven distinct vaccines and combining them for administration. Presently, only five of the seven serotypes are represented in the botulinum toxin vaccine. Further, some of the serotypes are composed of strains that do not produce high levels of toxin in culture. Thus, growth, purification and inactivation of the toxins for vaccine purposes is time consuming and expensive, owing to the high hazards associated with handling fully active toxin (Clayton et al. *Infection and Immunity* 1995 63(7):2738–2742). At this time this vaccine is only available through the Center of Disease Control for primarily experimental use.

Typically, botulism results from ingestion of food that is tainted with the toxin, or by the ingestion of food contaminated with organisms that can manufacture the toxin in the gut. Regardless of origin, botulinum toxin is synthesized as a relatively nontoxic single chain polypeptide with a molecular weight of approximately 150 kDa. To become fully toxic, it must undergo posttranslational processing, during which the molecule is cleaved by a protease to yield a dichain structure in which a heavy chain (approximately 100,000 daltons) is linked by a disulfide bond to a light chain (approximately 50,000 daltons). The dichain molecule is the holotoxin that accounts for biological activity. BoNT translocates from the gut into the general circulation (lymph and blood) wherein it is then distributed to cholinergic nerve endings which are the target sites of toxin action. The toxin enters these nerves, where it acts as a zinc-dependent endoprotease to cleave polypeptides that are essential for exocytosis (Montecucco, C. and Schiavo, G. *Mol. Microbiol.* 1994 13:1–8). Cleavage of these polypeptides leads to blockade of transmitter release and paralysis.

The heavy chain of the toxin is believed to be essential for binding and translocation of the toxin from the outside to the inside of the cholinergic nerve endings, while the light chain possesses the zinc-dependent endoprotease activity that accounts for the ability of the toxin to poison cholinergic nerve endings (Neimann et al. *Behring Inst. Mitt.* 1991 89:153–162). Accordingly, vaccines against botulism comprising a nontoxic 50 kDa carboxyterminal fragment of *Clostridium botulinum* have been described. LaPenotiere et al. *Toxicon* 1995 33(10):1383–6 and Clayton et al. *Infection and Immunity* 1995 63(7):2738–2742. Further, it has been suggested that this highly selective neurotoxin and tetanus toxin may be converted into nontoxic therapeutic tools that can be applied in delivery of drugs, hormones, enzymes or antiviral substances to the central nervous system.

SUMMARY OF THE INVENTION

An object of the present invention is to provide a modified botulinum toxin which maintains its ability to translocate from the gut into the general circulation but which is nontoxic. The modified botulinum toxin can be used as an oral vaccine for antigenic peptides including botulinum toxin and for the oral delivery of other therapeutic agents to the general circulation.

DETAILED DESCRIPTION OF THE INVENTION

One of the major challenges of modern medicine is the development of drugs that can be administered by the oral route. The development of oral peptide vaccines that evoke systemic immunity has proven to be especially problematic. Difficulties associated with the development of oral peptide vaccines include: degradation upon exposure to conditions of low pH and proteolytic enzymes found in the human gut; the antigenic domain of the agent which produces the illness being too large to allow for significant non-specific diffusion from the lumen of the gut to the general circulation; and an inability to design peptide vaccines that will bind exploitatively to receptors in the gut and undergo active transport to the general circulation. Despite these difficulties, considerable effort is being invested in the search for oral vaccines. For example, the concept of using engineered food such as a potato or a banana as a vector for widescale vaccination has recently been proposed. However, engineering the antigenic peptide into a food which is then ingested does not overcome these difficulties. Accordingly, there is a need for drug delivery vehicles which will reliably and reproducibly translocate an antigenic peptide or other therapeutic agent from the gut to the general circulation.

The present invention provides a modified botulinum toxin which can be used as an oral delivery vehicle for antigenic peptides including, but not limited to, botulinum toxin and other therapeutic agents to the general circulation. It has now been found that botulinum toxin translocates from the gut to the general circulation by binding to serospecific receptors on the mucosal side of polarized gut cells grown in a monolayer. Bound toxin is actively transported across the cells and delivered intact and unmodified on the serosal side of the monolayers. It has been suggested that auxiliary proteins such as hemagglutinin, which is a component of the non-covalent complex of proteins including the botulinum toxin which is released by Clostridium, may mediate binding and transport of the toxin across the gut wall. However, experiments performed with a recombinant form of the holotoxin now demonstrate that the botulinum toxin itself possesses the binding domain that recognizes receptors on the surface of gut cells. Further, it has now been demonstrated that modifications can be made to the light chain of the toxin to render it nontoxic without altering the capability of the protein to translocate from the gut to the general circulation. Accordingly, for the purposes of the present invention, by "modified botulinum toxin" is meant a botulinum toxin which maintains its capability of translocating from the gut to the general circulation but which is nontoxic. Alterations which will render the botulinum toxin nontoxic include mutations to the amino acid sequence of the light chain and deletion of the light chain or portions thereof. In a preferred embodiment, mutations are made to the zinc binding motif or the substrate binding motif of the light chain. For the purposes of this invention, by "nontoxic" it is meant that exposure of the cholinergic nerve endings to the modified botulinum toxin does not result in blockade of transmitter release in the nerve endings and paralysis. The effects of alterations rendering the botulinum toxin nontoxic on the ability of the toxin to translocate from the gut to the general circulation can be routinely performed in accordance with the teachings provided herein so that one of skill may identify modified botulinum toxins of the present invention. Included within this definition of modified botulinum toxins are botulinum toxins which further comprise a selected antigen for a protein other than botulinum toxin or a therapeutic agent.

For example, compositions were prepared comprising a botulinum neurotoxin in which the zinc binding motif of the light chain of the holotoxin was inactivated. The modified toxin is nontoxic because the holotoxin does not retain the ability to cause neuromuscular blockade, but the modification to the light chain does not adversely affect the ability of the remainder of the toxin molecule to escape the lumen of the gut into the general circulation. In this preferred embodiment at least three of the amino acids comprising the zinc binding motif of the light chain were modified. Specifically, the amino acids His (at position 229), Glu (at position 230), and His (at position 233) of the native sequence were substituted with amino acids Gly, Thr and Asn, respectively, resulting in SEQ ID NO: 1. The nucleic acid sequence encoding this modified botulinum toxin is depicted as SEQ ID NO: 2. These amino acid substitutions eliminated the ability of the holotoxin to bind catalytic zinc or other divalent cations.

Experiments have also been performed demonstrating that unnicked or single chain botulinum toxin also binds and is transported across the gut wall. Accordingly, modified botulinum toxins of the present invention also include compositions wherein the nicking site has been eliminated.

The biological activity of a modified botulinum toxin of the present invention was determined via an in vivo toxicity test, in vitro activity on the mouse phrenic nerve-hemidiaphragm preparation, and enzymatic activity in crude synaptosome preparations. For these experiments, the modified botulinum toxin, referred to herein as modified recombinant or modified rBoNT/C, was generated from botulinum toxin serotype C using site-directed mutagenesis to inactivate the zinc binding motif from the light chain of the holotoxin that is essential for endoprotease activity. However, other methods of peptide synthesis including, but not limited to, biochemical techniques, such as enzymatically cutting a peptide and cross linking the resulting fragments which are performed routinely by those of skill in the art can also be used. Further, given the structural and functional similarities of the botulism serotypes, one of skill could routinely prepare modified botulinum toxins from serotypes other than botulinum serotype C. For example, all serotypes of botulinum toxins are synthesized as relatively inactive precursors with molecular weights of approximately 150,000. In each case, the precursors must be "nicked" by a protease to generate a dichain molecule having a heavy chain (100,000 kDa) linked by a disulfide bond to a light chain (50,000 kDa). Every serotype of botulinum toxin acts preferentially on cholinergic nerve endings to block transmitter release, with the heavy chain acting principally as a tissue-targeting domain to direct the toxin to cholinergic nerve endings, and the light chain acting inside the nerve ending to block transmitter release. It is the light chain of every serotype that acts as a zinc-dependent metalloendoprotease to cleave one or more members of a family of polypeptides that is essential for transmitter release. In every serotype, there is a zinc binding motif, His-Glu-X-X-His (SEQ ID NO: 3) that is essential for enzymatic activity. Modification of the binding motif invariably causes loss of enzymatic activity. Further, alignment of the nucleic acid and amino acid sequences for a portion of each serotype encompassing the region of the zinc binding motif demonstrates a high degree of sequence identity in the regions adjacent to and comprising the zinc binding motif. Thus, examples using botulinum serotype C are representative of the entire class.

In vivo toxicity testing of modified rBoNT/C holotoxin demonstrated that the modified botulinum toxin with mutations in the zinc binding motif produced no acute toxicity in mice during a 16 week monitoring period following administration, even at high doses (10 $\mu$g per animal, i.p.). No apparent neurotoxicity or other obvious harmful effects were observed in any of the animals. In contrast, mice injected with 100 ng i.p. native BoNT/C died within 2 to 2.5 hours of injection.

The in vitro toxicity of modified BoNT/C holotoxin was also compared with that of native BoNT/C in mouse phrenic nerve-hemidiaphragm preparations. It was found that the addition of the modified botulinum toxin to phrenic nerve-hemidiaphragm preparations did not produce neuromuscular blockade ($1\times10^{-10}$ M; n=4). By contrast, addition of native BoNT/C ($1\times10^{-12}$ M; n=8) invariably produced paralysis of transmission (mean±S.E.M.=152±17 min).

The ability of this modified botulinum toxin to evoke an immune response was also tested after oral (p.o.) administration and subcutaneous (s.c.) injection. As determined by immunoblot analysis, both p.o. and s.c. administration of modified rBoNT/C holotoxin evoked systemic antibody production. Accordingly, the modified botulinum toxin of the present invention maintained its ability survive transit through the gut and to undergo active translocation out of the gut. This is further evidenced by the finding that s.c. administration of a non-homogeneous preparation of the modified botulinum toxin, which contained small amounts of unrelated proteins, is able to evoke an immune response against these unrelated proteins, while p.o. administration evoked antibody only against the modified botulinum toxin.

The protective effect of the antibodies elicited by p.o. and s.c. administration of the modified botulinum toxin was then demonstrated in both serum neutralization and in vivo toxicity tests. Regardless of the route of administration, serum from animals immunized with modified botulinum toxin inactivated a large dose (~10,000 $LD_{50}$) of native BoNT/C. Similarly, in in vivo toxicity tests, immunization with the modified botulinum toxin by either the p.o. or s.c. route produced a dramatic reduction in the potency of a subsequent injection of native toxin. Animals given the modified botulinum toxin by the oral route of administration had detectable antibodies in serum for at least three months. Further, animals that received the modified botulinum toxin either p.o. or s.c. were protected against native BoNT/C challenge three months after the third booster.

Accordingly, results from these experiments demonstrate that a modified botulinum toxin can be constructed in accordance with the teachings provided herein that is nontoxic but which retains the ability to translocate from the gut to the general circulation and to evoke protective antibodies. Further, compositions comprising a modified botulinum toxin of the present invention are clearly effective as oral vaccines against botulism in animals.

In addition, because the modified botulinum toxins of the present invention retain their ability to translocate from the gut and to be delivered intact to the general circulation, these modified botulinum toxins can be used as delivery vehicles for oral administration of antigens to proteins other than botulinum toxin and therapeutic agents to the general circulation. There are various ways in which the modified botulinum toxin could be used as a carrier for oral vaccines. For example, because the inactivation of the zinc binding motif of the light chain does not adversely affect the toxin's ability to translocate out of the gut, the zinc binding motif of the native botulinum toxin can be replaced with a selected antigen for a different protein, i.e. a protein other than botulism, to produce an oral vaccine against this different protein. Alternatively, well known techniques of protein chemistry and molecular biology can be used to attach the selected antigen or a portion thereof to a modified botulinum toxin. The resulting modified botulinum toxin would not only be nontoxic, but also retain its ability to translocate from the gut to the general circulation so that the selected antigen, when administered orally, would reach the general circulation to evoke a systemic immune response against the protein. Examples of vaccines which could be administered orally with the modified botulinum toxin include, but are not limited to, vaccines for Bacille Calmette-Guerin, cholera, diphtheria, hepatitis B, measles, meningitis, mumps, pertussis, plague, polio, rabies, rubella, tetanus, typhoid, and yellow fever. The oral vaccine can be administered individually or in combination, such as for DTP (diphtheria, tetanus, pertussis). The ability to deliver an oral vaccine is especially important for areas in which medical personnel are not readily available. Moreover, an oral vaccine of the present invention would represent an important economic advantage in addition to diminishing the need for skilled personnel as it would eliminate costs associated with syringes used for injection and/or for the disposal of used syringes.

Formulations of oral vaccines of the present invention preferably comprise the modified botulinum toxin in a pharmacologically acceptable carrier, such as sterile physiological saline, sterile saline with 0.1% gelatin, or sterile saline with 1.0 mg/ml bovine serum albumin. Alternatively, the modified botulinum toxin of the present invention can be genetically engineered into a plant so that food produced by the plant such as a potato or a banana can serve as a vector for widescale vaccination. Methods of genetically engineering plants to express a foreign peptide are well known in the art as exemplified by PCT/US96/09558, filed Jun. 6, 1996.

The modified botulinum toxins of the present invention are also useful in the construction of chimeric oral therapeutics. In this embodiment, a therapeutic agent can be linked to modified botulinum toxin to yield two broad groups of orally administered molecules: (1) new drugs with biologically stable linkages, and (2) conjugate prodrugs having biologically or chemically unstable linkages, which dissociate from the carrier upon reaching the blood. Examples of chimeric therapeutic techniques are described generally by Lautenslager, G. T. and Simpson, L. L., "Chimeric Molecules Constructed with Endogenous Substances," *Advances in Molecular and Cell Biology*, Vol. 9, pp. 233–262, JAI Press, Inc. (1994). For example, a therapeutic peptide could be attached to a modified botulinum toxin, thus creating an agent which possesses the characteristics of the substituent yet is capable of being administered orally. One example would be the creation of an orally administered thrombolytic agent. A fusion protein constructed by combining P-selectin and tissue plasminogen activator (TPA) is a promising chimera which expresses thrombolytic activity and targets to the thrombi. This chimera must be introduced into the blood stream. However, using either molecular biology or protein chemistry, this 'first order' chimeric molecule could be attached to a modified botulinum toxin of the present invention to create a higher order chimera which possesses the added advantage of being delivered to the general circulation by oral administration. Another example is in the design of an orally administered anti-neoplastic drug. Various antineoplastic drugs which exploit the cytotoxic properties of one molecule, fused to a portion of another which functions to specifically target the toxin have been disclosed. A more recent example employs the amino-terminus of *Pseudomonas exotoxin* (PE) fused to epidermal growth factor (EGF), resulting in chimera EGF-PE which can be used as a cytotoxic agent towards EGF-receptor-bearing cancer cells. Linkage of this chimera to a modified botulinum toxin of the present invention would result in creation of a higher order chimera which can be administered orally.

The general concepts for use of a modified botulinum toxin as a carrier for vaccines or other therapeutic agents are the same for human and for non-human animals, with one exception. All serotypes of botulinum toxin are not likely to be equally efficacious as carriers for drugs in all species. Clinical evidence suggests that humans are especially sensitive to the effects of serotypes A, B, and E. This may relate to the efficiency with which these three serotypes are absorbed from the gastrointestinal system. Thus, serotypes A, B, and E would be preferred carriers of therapeutic agents for humans.

On the contrary, most non-human animals are particularly sensitive to serotype C. This suggests that as to veterinary medicine, the preferred carrier of therapeutic agents for non-human animal use would be serotype C. Examples of animal vaccines which could be administered orally with the modified botulinum toxin include, but are not limited to, ones for adenovirus type 2, *Bordetella bronchispetica*, botulism, calicivirus, *Chlamydia psittaci*, clostridial diseases, such as *Clostridium Perfringens* type C, coronaviruses, distemper, equine encephalomyelitis,

*Escherichia coli*, feline infectious peritonitis, feline leukemia virus, feline panleukopenia, hepatitis, leptospirosis, parainfluenza virus, parvoviruses, rabies, rhinotracheitis virus, and tetanus.

The following examples are provided for illustrative purposes only and are not intended to limit the invention.

EXAMPLES

Restriction endonucleases and DNA modifying enzymes were purchased from New England Biolabs (Beverly, Mass.). The expression vector pQE-30 and nickel-nitrilotriacetic acid (Ni-NTA) Agarose were purchased from QIAGEN (Chatsworth, Calif.). Monoclonal antibodies (mab) specific for the 6xHis affinity tag were purchased from QIAGEN. Anti-syntaxin mAbs (S-0664; anti-HPC-1) were purchased from SIGMA (St. Louis, Mo.), and horse anti-BoNT/C antibodies was obtained from the Centers for Disease Control (CDC, Atlanta, Ga.). Plasmids pCL8 and pCH3 carrying EcoRI fragments of BoNT/C DNA have been described previously by Kimura et al. *BBRC* 1990 171:1304–1311.

Figure 1:
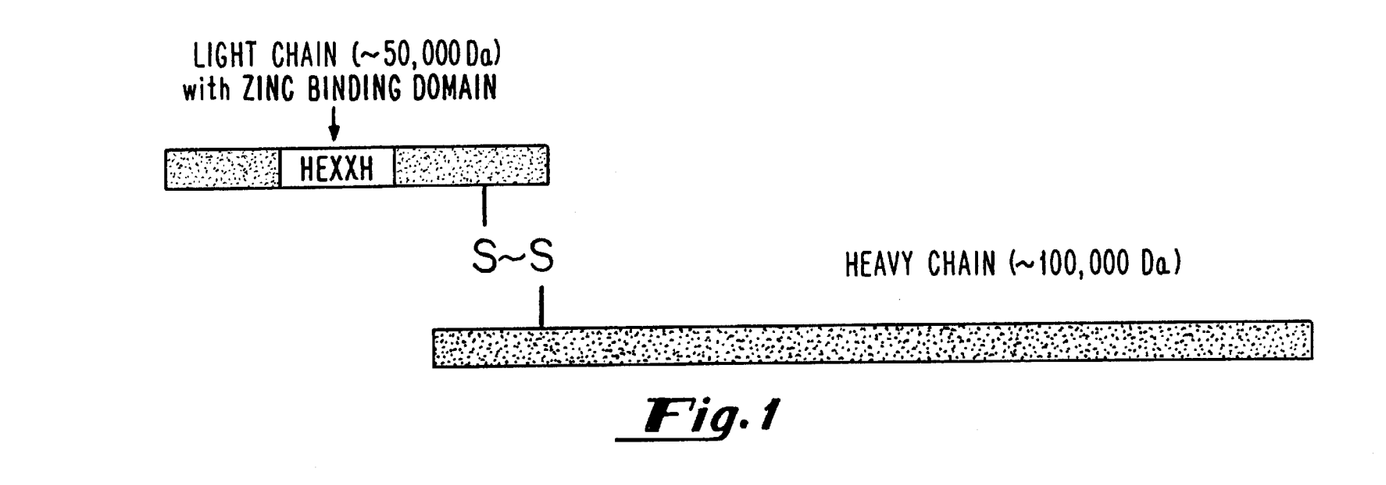
FIG. 1 is diagram of the native botulinum toxin. This figure illustrates the light chain with the zinc binding motif linked by a disulfide bond to the heavy chain of the native toxin.
Figure 2:
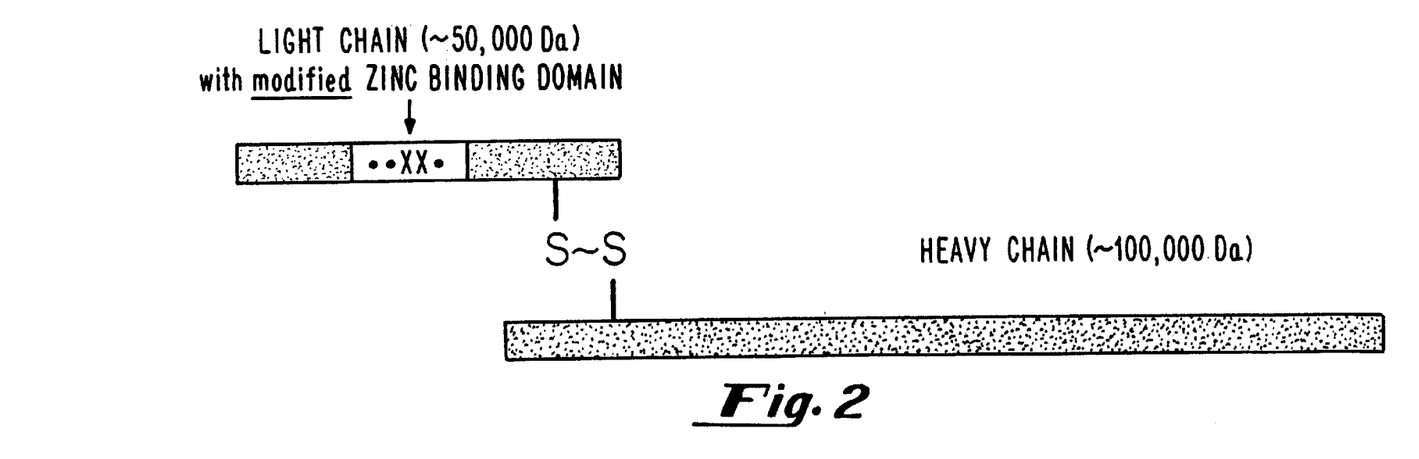
FIG. 2 is a diagram illustrating an example of a modified botulinum toxin of the present invention. This figure illustrates the light chain with a modified zinc binding motif linked to the intact heavy chain of botulinum toxin.

Example 1
Construction of expression vectors for synthesis rBoNT/C holotoxin A schematic representation of the native botulinum toxin is depicted in FIG. 1. A schematic representation of a modified botulinum toxin, rBoNT/C is depicted in FIG. 2. The nucleic acid and protein sequences for the modified botulinum toxin, rBoNT/C are depicted in SEQ ID NO: 2 and SEQ ID NO: 1, respectively.

Techniques for DNA fragment isolation, repair of overhanging ends with the Klenow fragment of DNA polymerase I, and ligation with T4 ligase are known to those skilled in the art and have been described, for example, by Sambrook et al., 1989 *Molecular Cloning: A Laboratory Manual,* 2nd ed., Cold Spring Harbor Laboratory Press, Cold Spring Harbor, N.Y. All cloning steps and expression were performed in *Escherichia coli* strain M-15 (QIAGEN) containing the pREP4 repressor plasmid.

The gene encoding a recombinant modified botulinum toxin was assembled from three separate toxin fragments (fragments I, II and III) generated using PCR and ligated into vector pQE-30 resulting in plasmid pQE-TC1. Initially, a DNA fragment coding for the amino-terminal portion of BoNT/C (fragments I and II) was amplified from plasmid pCL8 in two sequential steps to generate pBot C2. DNA fragment I (nt 4–689) was amplified using the following pair of oligonucleotide primers:
(forward) 5'-CCCAATAACAATTAACAACTTTAAT-3' (SEQ ID NO: 4)
KpnI
(reverse) 5'-TTTGGTACCCATTAAAATTAGTATTGGATCCAT-3' (SEQ ID NO: 5)

One cytosine was added to the 5'-end of the forward primer to provide for reconstruction of the BamHI restriction site, as well as to clone rBoNT/C DNA in frame with the pQE-30 initiation of translation methionine.

A KpnI restriction site was included in the reverse primer to generate amino acid mutations His$^{229}$→Gly and Glu$^{230}$→Thr at the 3' end of fragment I. Amplified fragment I was treated with T4 polymerase, cut with KpnI and inserted between the Klenow filled-in BamHI and KpnI sites of the expression vector pQE-30, resulting in plasmid pBot C1. DNA fragment II (nt 689–1633) was then amplified using oligonucleotide primers:

KpnI
(forward) 5'-TTTGGTACCCTTAATAATGCAATGCATAATTTATATGGA-3' (SEQ ID NO: 6)
EcoRI
(reverse) 5'-GAATTCAAATAATCAACATTTTGAG-3' (SEQ ID NO: 7)

In the forward primer nucleotide changes were introduced to create a KpnI site and generate amino acid mutations His$^{229}$→Gly, Glu$^{230}$→Thr, and His$^{233}$→Asn at the 5' end of fragment II. The reverse primer was complementary to the BoNT/C sequence and contained an internal EcoRI site at nucleotide position 1633. Amplified fragment II was treated with T4 polymerase, cut with KpnI and inserted between the KpnI and Klenow filled-in SalI sites of pBot C1. The resulting plasmid pBot C2 contained the 5'-terminal fragment of BoNT/C (nt 4–1633) in frame with the ATG codon and 6xHis affinity sequence of pQE-30.

DNA fragment III (nt 1633–3873) coding for the carboxy-terminal domain of BoNT/C was amplified from plasmid pCH3 using oligonucleotide primers
EcoRI
forward 5'-TTTGAATTCTTATTATTACCTAGAATC-3' (SEQ ID NO: 8)
SacI
reverse 5'-TTTGAGCTCTTATTCACTTACAGGTACAAAAC-3' (SEQ ID NO: 9)

The forward primer was complementary to the BoNT/C sequence and contained an internal EcoRI site at position 1632. In the reverse primer, a SacI restriction site was introduced immediately downstream of the stop codon. Amplified fragment III was digested with EcoRI and SacI and cloned separately into EcoRI and SacI digested plasmid pQE-30 generating plasmid pBot C3. Finally, the DNA encoding a full-size, modified botulinum toxin was reconstructed by introducing the EcoRI—EcoRI fragment (nt –88 to +1632) from plasmid pBot C2 into EcoRI digested, calf intestine alkaline phosphatase dephosphorylated plasmid pBot C3 to give plasmid pQE-TC1. All PCR fragments were reanalyzed by DNA sequencing.

The oligonucleotide primers were designed to engineer a KpnI restriction site in the segment of DNA encoding the zinc-binding motif. The creation of the KpnI restriction site in this DNA segment enabled the mutation of three amino acids (His$^{229}$→Gly; Glu$^{230}$→Thr and His$^{233}$→Asn) that are essential for zinc binding, and provided for the reconstruction of a DNA encoding a modified botulinum toxin without preliminary cloning of wild type BoNT/C DNA. The recombinant modified botulinum toxin, synthesized from plasmid pQE-TC1, contained eleven additional amino acids, Arg-Gly-Ser-His-His-His-His-His-His-Gly-Ser (SEQ ID NO: 10), at the amino-terminus.

Example 2
Optimization of neurotoxin expression

PCR was used to modify a sequence of the pQE-30 vector preceding the structural gene encoding modified rBoNT/C. A new forward primer, 5'-CGGTACCATGCCAATAACAATTAACAACTTT-3' (SEQ ID NO: 11), containing ten additional nucleotides on the 5' -end and a new reverse primer,
BglII
5'-AGCTATAGATCTATAATAATCCAA-3' (SEQ ID NO: 12) covering the BglII restriction site at position 892 of the BoNT/C sequence (Kimura et al. *Biochem. Biophys. Res. Comm.* 1990 171:1304–1311) were used to reamplify a DNA fragment coding for the amino-terminal portion of the rBoNT/C. The amplified fragment was treated with T4 polymerase, cut with BglII and inserted between the Klenow filled in BamHI and BglII sites of pQE-TC1 to give plasmid pQE-TC2.

Example 3
Expression and purification of modified rBoNT/C holotoxin

Cultures were grown in Lennox L broth at 37° C., with shaking, to an $A_{600}$ of 0.6–0.8. Isopropyl-β-D-thiogalactopyranoside was added to 1.0 mM final concentration, and incubation continued for an additional 5 hours. Bacteria from 1 liter of induced culture were harvested by centrifugation at 4° C. and resuspended in 20 ml of 50 mM sodium phosphate buffer, pH 7.4, with 300 mM NaCl. The cell suspension was lysed, on ice, by sonication, with 2 pulses of 1 minute duration each at 75% power, using a Model 60 Sonic Dismembrator (Fisher Scientific, Malvern, Pa.). Lysates were centrifuged at 20,000×g for 30 minutes at 4° C. The clarified supernatants were mixed with 1 ml of packed Ni-NTA resin, incubated for 1 hour at 4° C. on a rotator and finally poured into a 25 ml column. The column was washed with 30 volumes of washing buffer (50 mM sodium phosphate, pH 6.0, 300 mM NaCl, 25 mM imidazole). Bound proteins were eluted with elution buffer (50 mM sodium phosphate, pH 4.5, 300 mM NaCl). Purified proteins were analyzed on sodium dodecylsulfate polyacrylamide gels (SDS-PAGE).

Example 4
Immunoblot Analysis

The ability of *E. coli* to drive expression of a recombinant modified botulinum toxin from plasmid pQE-TC1 was examined by immunoblot analysis of cell extract. Proteins for analysis by Western blotting were separated on 10% polyacrylamide gels according to the method of Laemmli, U.K. *Nature* 1970 22:680–685, transferred to nitrocellulose, and processed for detection of immunoreactive proteins containing the 6xHis affinity tag. Incubations with primary antibodies were performed for 1 hour at 37° C. with a 1:2000 dilution of the anti-6xHis affinity tag mAb, or with anti-BoNT/C antibodies. Membranes were developed using enhanced chemiluminescence according to manufacturers instructions (ECL; Amersham Corp., Arlington Heights, Ill.). The synthesis of recombinant proteins was induced with IPTG and aliquots of solubilized cells were run on SDS-PAGE.

Western blot analysis with anti-6xHis tag or anti-BoNT/C antibodies revealed an extremely low level of expression. Accordingly, a new plasmid was constructed which did not contain the stretch of four cytosine nucleotides which originated from cloning of neurotoxin DNA into the BamHI site of pQE-30 vector and designated pQE-TC2. Western blot analysis with anti-6xHis tag antibody revealed that pQE-TC2 was more efficient at driving the synthesis of modified rBoNT/C holotoxin. Indeed, 1–2 mg of modified rBoNT/C holotoxin could be purified from 1L of Lennox broth.

Modified rBoNT/C holotoxin was synthesized in soluble form, without visible degradation, but unlike *Clostridium botulinum* the *E. coli* did not provide for efficient nicking of modified rBoNT/C holotoxin. Only trace amounts of L-chain were detectable in modified rBoNT/C holotoxin by Coomassie staining or Western blotting. However, modified rBoNT/C holotoxin was efficiently nicked with immobilized TPCK-trypsin (Pierce, Rockford, Ill.) and produced heavy and light chains of the correct molecular weight. Modified rBoNT/C holotoxin synthesized from pQE-TC2 contained fourteen additional amino acids (Arg-Gly-Ser-His-His-His-His-His-His-Gly-Ser-Gly-Thr (SEQ ID NO: 13)) at the amino terminus. The 6xHis sequence within this fourteen amino acid segment was used for purification and subsequent detection of synthesized protein. The recombinant protein produced in this manner was purified by affinity chromatography on Ni-NTA resin using the 6xHis affinity tag. Specifically bound protein was eluted with low pH (elution buffer pH 4.5) and analyzed on SDS-PAGE. Analysis of protein eluted from the affinity resin revealed that toxin could be purified to a homogeneity of 80%–90%. The purified modified recombinant BoNT/C or modified rBoNT/C was used for all studies presented herein.

Example 5
Bioassay of recombinant proteins

As described in the examples that follow, the purified recombinant proteins was assayed for biological activity using an in vivo toxicity test, in vitro activity on the mouse phrenic nerve-hemidiaphragm preparation, and enzymatic activity in crude synaptosome preparations.

A. In vivo toxicity testing

The toxicity of modified rBoNT/C holotoxin was tested. Modified rBoNT/C holotoxin purified by elution from the histidine affinity resin was diluted in PBS including 1 mg/ml BSA and injected intraperitoneally (i.p.) into mice. The rBoNT/C holotoxin was administered in a 100 μl aliquot of PBS-BSA at a concentration of 10 μg per animal having an average weight of 25 g. The animals were monitored for a total of 16 weeks to rule out any non-specific toxicity.

B. In vitro toxicity testing

Toxicity was bioassayed on the mouse phrenic nerve-hemidiaphragm preparations using the method of Simpson et al. *J. Pharmacol. Exp. Ther.* 1990 254:98–103. Tissues were excised and suspended in physiological buffer that was aerated with 95% $O_2$, 5% $CO_2$ and maintained at 35° C. The physiological solution had the following composition (millimolar): NaCl, 137; KCl, 5; $CaCl_2$, 1.8; $MgSO_4$, 1.0; $NaHCO_3$, 24; $NaH_2PO_4$, 1.0; D-glucose, 11; and gelatin, 0.01%. Phrenic nerves were stimulated continuously (1.0 Hz; 0.1–0.3 millisecond duration), and muscle twitch was recorded. Toxin-induced paralysis was measured as a 50% reduction in muscle twitch response to neurogenic stimulation.

C. Cleavage of substrate

Synaptosomes (1 mg/ml) were prepared according to the method of Rosahl et al. *Cell* 1993 75:661–670. The synaptosomes were incubated in the presence of modified rBoNT/C holotoxin (100 nM) for 90 minutes at 37° C. in Tris-buffered saline (TBS) or in TBS containing 10 mM dithiothreitol. In parallel experiments, synaptosomal membranes were incubated in the presence and absence of native BoNT/C. The proteins were separated on 15% SDS-PAGE, transferred to nitrocellulase, and processed for detection of immunoreactive proteins with anti-syntaxin mAb.

Example 6
Serum antibody response in mice immunized with modified rBoNT/C holotoxin Swiss-Webster female mice weighing approximately 25 grams (Ace Animals, Boyertown, Pa.) were immunized in parallel experiments either, s.c. or p.o., with rBoNt/C holotoxin or TBS, to assess the ability of this peptide to evoke a serum immune response.

A. Immunization and sample collection

For s.c. injection each animal received 2 μg protein in 0.1 ml of elution buffer. For the oral administration route, each animal was fed 4 μg of protein in 0.2 ml elution buffer administered through an intragastric feeding needle. Mice were immunized on day zero, and boosters were given on days 14, 28, and 42. Samples of serum from identically immunized mice were collected and pooled on days 21, 35, and 49 after immunization. For collection of serum, mice were bled with heparinized capillary tubes at the retro-orbital plexus while under isoflurane anesthesia.

B. Assay of serum for antibody production

Sera from immunized or control mice were assayed for antibodies using immunoblot analysis for immunoreactivity to unnicked modified botulinum toxin. Recombinant antigen (modified botulinum toxin; 0.1 µg/lane) was separated by SDS-PAGE and transferred to nitrocellulose membranes. Membranes were blocked with 5% non-fat powdered milk in TBS, cut into strips and processed for detection of immunoreactive proteins using various serum samples. Primary incubations were performed overnight (18 hours) at room temperature with a 1:1000 diluted serum. A secondary horseradish peroxidase-labeled anti-mouse IgG was used at a 1:10,000 dilution for 1 hour at room temperature. After extensive washing, membranes were developed using ECL (Amersham).

Example 7

Neutralizing activity of serum from immunized mice

Experiments were performed to assess the ability of various serum samples to neutralize native BoNT/C. Three different sources of serum were tested, as follows: 1) non-immune serum, 2) serum from animals that had received modified rBoNT/C holotoxin p.o., and 3) serum from animals that had received modified rBoNT/C holotoxin s.c. Native BoNT/C (10 µl, 100 ng) was incubated with 10 µl of pre-immune or immune serum at 37° C. for 1 hour, or with PBS-BSA. Subsequently, the incubation mixture was diluted with 80 Al PBS including 1 mg/ml BSA and injected i.p. The mice were monitored for 48 hours to assess any residual toxicity of the various mixtures.

Example 8

Protection of mice against challenge with native BoNT/C

Three months after administration of the third booster, mice immunized with rBoNT/C were challenged with an i.p. dose of 100 ng native BoNT/C per animal. The survival of challenged animals was monitored for 5 days.

The disclosures of each and every, patent, patent application, and publication cited herein are hereby incorporated herein by reference in their entirety.

While the invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A modified botulinum toxin comprising a botulinum toxin capable of translocating from the gut to the general circulation and a selected antigen, wherein said botulinum toxin is altered to be nontoxic by mutating or deleting amino acids in the light chain of the botulinum toxin.

2. A method of protecting an animal against botulism comprising administering orally to an animal a modified botulinum toxin and a pharmaceutically acceptable vehicle, wherein said botulinum toxin is altered to be nontoxic by mutating or deleting amino acids in the light chain of the botulinum toxin.

* * * * *

SEQUENCE LISTING (1) GENERAL INFORMATION:

(iii) NUMBER OF SEQUENCES: 13

(2) INFORMATION FOR SEQ ID NO: 1:

(i) SEQUENCE CHARACTERISTICS:
        (A) LENGTH: 1291
        (B) TYPE: AMINO ACID
        (D) TOPOLOGY: LINEAR (xi) SEQUENCE DESCRIPTION: SEQ ID NO: 1:

Met Pro Ile Thr Ile Asn Asn Phe Asn Tyr Ser Asp Pro Val Asp
 1               5                  10                  15

Asn Lys Asn Ile Leu Tyr Leu Asp Thr His Leu Asn Thr Leu Ala
                20                  25                  30

Asn Glu Pro Glu Lys Ala Phe Arg Ile Thr Gly Asn Ile Trp Val
                35                  40                  45

Ile Pro Asp Arg Phe Ser Arg Asn Ser Asn Pro Asn Leu Asn Lys
                50                  55                  60

Pro Pro Arg Val Thr Ser Pro Lys Ser Gly Tyr Tyr Asp Pro Asn
                65                  70                  75

Tyr Leu Ser Thr Asp Ser Asp Lys Asp Thr Phe Leu Lys Glu Ile
                80                  85                  90

Ile Lys Leu Phe Lys Arg Ile Asn Ser Arg Glu Ile Gly Glu Glu
                95                 100                 105

Leu Ile Tyr Arg Leu Ser Thr Asp Ile Pro Phe Pro Gly Asn Asn
               110                 115                 120

Asn Thr Pro Ile Asn Thr Phe Asp Phe Asp Val Asp Phe Asn Ser
               125                 130                 135

-continued

Val Asp Val Lys Thr Arg Gln Gly Asn Asn Trp Val Lys Thr Gly
            140                 145                 150

Ser Ile Asn Pro Ser Val Ile Ile Thr Gly Pro Arg Glu Asn Ile
            155                 160                 165

Ile Asp Pro Glu Thr Ser Thr Phe Lys Leu Thr Asn Asn Thr Phe
            170                 175                 180

Ala Ala Gln Glu Gly Phe Gly Ala Leu Ser Ile Ile Ser Ile Ser
            185                 190                 195

Pro Arg Phe Met Leu Thr Tyr Ser Asn Ala Thr Asn Asp Val Gly
            200                 205                 210

Glu Gly Arg Phe Ser Lys Ser Glu Phe Cys Met Asp Pro Ile Leu
            215                 220                 225

Ile Leu Met Gly Thr Leu Asn Asn Ala Met His Asn Leu Tyr Gly
            230                 235                 240

Ile Ala Ile Pro Asn Asp Gln Thr Ile Ser Ser Val Thr Ser Asn
            245                 250                 255

Ile Phe Tyr Ser Gln Tyr Asn Val Lys Leu Glu Tyr Ala Glu Ile
            260                 265                 270

Tyr Ala Phe Gly Gly Pro Thr Ile Asp Leu Ile Pro Lys Ser Ala
            275                 280                 285

Arg Lys Tyr Phe Glu Glu Lys Ala Leu Asp Tyr Tyr Arg Ser Ile
            290                 295                 300

Ala Lys Arg Leu Asn Ser Ile Thr Thr Ala Asn Pro Ser Ser Phe
            305                 310                 315

Asn Lys Tyr Ile Gly Glu Tyr Lys Gln Lys Leu Ile Arg Lys Tyr
            320                 325                 330

Arg Phe Val Val Glu Ser Ser Gly Glu Val Thr Val Asn Arg Asn
            335                 340                 345

Lys Phe Val Glu Leu Tyr Asn Glu Leu Thr Gln Ile Phe Thr Glu
            350                 355                 360

Phe Asn Tyr Ala Lys Ile Tyr Asn Val Gln Asn Arg Lys Ile Tyr
            365                 370                 375

Leu Ser Asn Val Tyr Thr Pro Val Thr Ala Asn Ile Leu Asp Asp
            380                 385                 390

Asn Val Tyr Asp Ile Gln Asn Gly Phe Asn Ile Pro Lys Ser Asn
            395                 400                 405

Leu Asn Val Leu Phe Met Gly Gln Asn Leu Ser Arg Asn Pro Ala
            410                 415                 420

Leu Arg Lys Val Asn Pro Glu Asn Met Leu Tyr Leu Phe Thr Lys
            425                 430                 435

Phe Cys His Lys Ala Ile Asp Gly Arg Ser Leu Tyr Asn Lys Thr
            440                 445                 450

Leu Asp Cys Arg Glu Leu Leu Val Lys Asn Thr Asp Leu Pro Phe
            455                 460                 465

Ile Gly Asp Ile Ser Asp Val Lys Thr Asp Ile Phe Leu Arg Lys
            470                 475                 480

Asp Ile Asn Glu Glu Thr Glu Val Ile Tyr Tyr Pro Asp Asn Val
            485                 490                 495

Ser Val Asp Gln Val Ile Leu Ser Lys Asn Thr Ser Glu His Gly
            500                 505                 510

Gln Leu Asp Leu Leu Tyr Pro Ser Ile Asp Ser Glu Ser Glu Ile
            515                 520                 525

Leu Pro Gly Glu Asn Gln Val Phe Tyr Asp Asn Arg Thr Gln Asn

-continued

```
                530                 535                 540
Val Asp Tyr Leu Asn Ser Tyr Tyr Leu Glu Ser Gln Lys Leu
                545                 550                 555
Ser Asp Asn Val Glu Asp Phe Thr Phe Thr Arg Ser Ile Glu Glu
                560                 565                 570
Ala Leu Asp Asn Ser Ala Lys Val Tyr Thr Tyr Phe Pro Thr Leu
                575                 580                 585
Ala Asn Lys Val Asn Ala Gly Val Gln Gly Gly Leu Phe Leu Met
                590                 595                 600
Trp Ala Asn Asp Val Val Glu Asp Phe Thr Thr Asn Ile Leu Arg
                605                 610                 615
Lys Asp Thr Leu Asp Lys Ile Ser Asp Val Ser Ala Ile Ile Pro
                620                 625                 630
Tyr Ile Gly Pro Ala Leu Asn Ile Ser Asn Ser Val Arg Arg Gly
                635                 640                 645
Asn Phe Thr Glu Ala Phe Ala Val Thr Gly Val Thr Ile Leu Leu
                650                 655                 660
Glu Ala Phe Pro Glu Phe Thr Ile Pro Ala Leu Gly Ala Phe Val
                665                 670                 675
Ile Tyr Ser Lys Val Gln Glu Arg Asn Glu Ile Ile Lys Thr Ile
                680                 685                 690
Asp Asn Cys Leu Glu Gln Arg Ile Lys Arg Trp Lys Asp Ser Tyr
                695                 700                 705
Glu Trp Met Met Gly Thr Trp Leu Ser Arg Ile Ile Thr Gln Phe
                710                 715                 720
Asn Asn Ile Ser Tyr Gln Met Tyr Asp Ser Leu Asn Tyr Gln Ala
                725                 730                 735
Gly Ala Ile Lys Ala Lys Ile Asp Leu Glu Tyr Lys Lys Tyr Ser
                740                 745                 750
Gly Ser Asp Lys Glu Asn Ile Lys Ser Gln Val Glu Asn Leu Lys
                755                 760                 765
Asn Ser Leu Asp Val Lys Ile Ser Glu Ala Met Asn Asn Ile Asn
                770                 775                 780
Lys Phe Ile Arg Glu Cys Ser Val Thr Tyr Leu Phe Lys Asn Met
                785                 790                 795
Leu Pro Lys Val Ile Asp Glu Leu Asn Glu Phe Asp Arg Asn Thr
                800                 805                 810
Lys Ala Lys Leu Ile Asn Leu Ile Asp Ser His Asn Ile Ile Leu
                815                 820                 825
Val Gly Glu Val Asp Lys Leu Lys Ala Lys Val Asn Asn Ser Phe
                830                 835                 840
Gln Asn Thr Ile Pro Phe Asn Ile Phe Ser Tyr Thr Asn Asn Ser
                845                 850                 855
Leu Leu Lys Asp Ile Ile Asn Glu Tyr Phe Asn Asn Ile Asn Asp
                860                 865                 870
Ser Lys Ile Leu Ser Leu Gln Asn Arg Lys Asn Thr Leu Val Asp
                875                 880                 885
Thr Ser Gly Tyr Asn Ala Glu Val Ser Glu Glu Gly Asp Val Gln
                890                 895                 900
Leu Asn Pro Ile Phe Pro Phe Asp Phe Lys Leu Gly Ser Ser Gly
                905                 910                 915
Glu Asp Arg Gly Lys Val Ile Val Thr Gln Asn Glu Asn Ile Val
                920                 925                 930
```

-continued

```
Tyr Asn Ser Met Tyr Glu Ser Phe Ser Ile Ser Phe Trp Ile Arg
            935                 940                 945

Ile Asn Lys Trp Val Ser Asn Leu Pro Gly Tyr Thr Ile Ile Asp
            950                 955                 960

Ser Val Lys Asn Asn Ser Gly Trp Ser Ile Gly Ile Ile Ser Asn
            965                 970                 975

Phe Leu Val Phe Thr Leu Lys Gln Asn Glu Asp Ser Glu Gln Ser
            980                 985                 990

Ile Asn Phe Ser Tyr Asp Ile Ser Asn Asn Ala Pro Gly Tyr Asn
            995                 1000                1005

Lys Trp Phe Phe Val Thr Val Thr Asn Asn Met Met Gly Asn Met
            1010                1015                1020

Lys Ile Tyr Ile Asn Gly Lys Leu Ile Asp Thr Ile Lys Val Lys
            1025                1030                1035

Glu Leu Thr Gly Ile Asn Phe Ser Lys Thr Ile Thr Phe Glu Ile
            1040                1045                1050

Asn Lys Ile Pro Asp Thr Gly Leu Ile Thr Ser Asp Ser Asp Asn
            1055                1060                1065

Ile Asn Met Trp Ile Arg Asp Phe Tyr Ile Phe Ala Lys Glu Leu
            1070                1075                1080

Asp Gly Lys Asp Ile Asn Ile Leu Phe Asn Ser Leu Gln Tyr Thr
            1085                1090                1095

Asn Val Val Lys Asp Tyr Trp Gly Asn Asp Leu Arg Tyr Asn Lys
            1100                1105                1110

Glu Tyr Tyr Met Val Asn Ile Asp Tyr Leu Asn Arg Tyr Met Tyr
            1115                1120                1125

Ala Asn Ser Arg Gln Ile Val Phe Asn Thr Arg Arg Asn Asn Asn
            1130                1135                1140

Asp Phe Asn Glu Gly Tyr Lys Ile Ile Ile Lys Arg Ile Arg Gly
            1145                1150                1155

Asn Thr Asn Asp Thr Arg Val Arg Gly Gly Asp Ile Leu Tyr Phe
            1160                1165                1170

Asp Met Thr Ile Asn Asn Lys Ala Tyr Asn Leu Phe Met Lys Asn
            1175                1180                1185

Glu Thr Met Tyr Ala Asp Asn His Ser Thr Glu Asp Ile Tyr Ala
            1190                1195                1200

Ile Gly Leu Arg Glu Gln Thr Lys Asp Ile Asn Asp Asn Ile Ile
            1205                1210                1215

Phe Gln Ile Gln Pro Met Asn Asn Thr Tyr Tyr Tyr Ala Ser Gln
            1220                1225                1230

Ile Phe Lys Ser Asn Phe Asn Gly Glu Asn Ile Ser Gly Ile Cys
            1235                1240                1245

Ser Ile Gly Thr Tyr Arg Phe Arg Leu Gly Gly Asp Trp Tyr Arg
            1250                1255                1260

His Asn Tyr Leu Val Pro Thr Val Lys Gln Gly Asn Tyr Ala Ser
            1265                1270                1275

Leu Leu Glu Ser Thr Ser Thr His Trp Gly Phe Val Pro Val Ser
            1280                1285                1290

Glu
```

(2) INFORMATION FOR SEQ ID NO: 2:

(i) SEQUENCE CHARACTERISTICS:

(A) LENGTH: 3950
(B) TYPE: NUCLEIC ACID
(C) STRANDEDNESS: SINGLE
(D) TOPOLOGY: LINEAR (iv) ANTI-SENSE: NO (xi) SEQUENCE DESCRIPTION: SEQ ID NO: 2:

| | | | | |
|---|---|---|---|---|
| GGATATTAGA | AAGTTAGGAG | ATGTTAGTAT | TATGCCAATA | ACAATTAACA | 50 |
| ACTTTAATTA | TTCAGATCCT | GTTGATAATA | AAAATATTTT | ATATTTAGAT | 100 |
| ACTCATTTAA | ATACACTAGC | TAATGAGCCT | GAAAAAGCCT | TTCGCATTAC | 150 |
| AGGAAATATA | TGGGTAATAC | CTGATAGATT | TTCAAGAAAT | TCTAATCCAA | 200 |
| ATTTAAATAA | ACCTCCTCGA | GTTACAAGCC | CTAAAAGTGG | TTATTATGAT | 250 |
| CCTAATTATT | TGAGTACTGA | TTCTGACAAA | GATACATTTT | TAAAAGAAAT | 300 |
| TATAAAGTTA | TTTAAAAGAA | TTAATTCTAG | AGAAATAGGA | GAAGAATTAA | 350 |
| TATATAGACT | TTCGACAGAT | ATACCCTTTC | CTGGGAATAA | CAATACTCCA | 400 |
| ATTAATACTT | TTGATTTTGA | TGTAGATTTT | AACAGTGTTG | ATGTTAAAAC | 450 |
| TAGACAAGGT | AACAACTGGG | TTAAAACTGG | TAGCATAAAT | CCTAGTGTTA | 500 |
| TAATAACTGG | ACCTAGAGAA | AACATTATAG | ATCCAGAAAC | TTCTACGTTT | 550 |
| AAATTAACTA | ACAATACTTT | TGCGGCACAA | GAAGGATTTG | GTGCTTTATC | 600 |
| AATAATTTCA | ATATCACCTA | GATTTATGCT | AACATATAGT | AATGCAACTA | 650 |
| ATGATGTAGG | AGAGGGTAGA | TTTTCTAAGT | CTGAATTTTG | CATGGATCCA | 700 |
| ATACTAATTT | TAATGGGTAC | CCTTAATAAT | GCAATGCATA | ATTTATATGG | 750 |
| AATAGCTATA | CCAAATGATC | AAACAATTTC | ATCTGTAACT | AGTAATATTT | 800 |
| TTTATTCTCA | ATATAATGTG | AAATTAGAGT | ATGCAGAAAT | ATATGCATTT | 850 |
| GGAGGTCCAA | CTATAGACCT | TATTCCTAAA | AGTGCAAGGA | AATATTTTGA | 900 |
| GGAAAAGGCA | TTGGATTATT | ATAGATCTAT | AGCTAAAAGA | CTTAATAGTA | 950 |
| TAACTACTGC | AAATCCTTCA | AGCTTTAATA | AATATATAGG | GGAATATAAA | 1000 |
| CAGAAACTTA | TTAGAAAGTA | TAGATTCGTA | GTAGAATCTT | CAGGTGAAGT | 1050 |
| TACAGTAAAT | CGTAATAAGT | TTGTTGAGTT | ATATAATGAA | CTTACACAAA | 1100 |
| TATTTACAGA | ATTTAACTAC | GCTAAAATAT | ATAATGTACA | AAATAGGAAA | 1150 |
| ATATATCTTT | CAAATGTATA | TACTCCGGTT | ACGGCGAATA | TATTAGACGA | 1200 |
| TAATGTTTAT | GATATACAAA | ATGGATTTAA | TATACCTAAA | AGTAATTTAA | 1250 |
| ATGTACTATT | TATGGGTCAA | AATTTATCTC | GAAATCCAGC | ATTAAGAAAA | 1300 |
| GTCAATCCTG | AAAATATGCT | TTATTTATTT | ACAAAATTTT | GTCATAAAGC | 1350 |
| AATAGATGGT | AGATCATTAT | ATAATAAAAC | ATTAGATTGT | AGAGAGCTTT | 1400 |
| TAGTTAAAAA | TACTGACTTA | CCCTTTATAG | GTGATATTAG | TGATGTTAAA | 1450 |
| ACTGATATAT | TTTAAGAAA | AGATATTAAT | GAAGAAACTG | AAGTTATATA | 1500 |
| CTATCCGGAC | AATGTTTCAG | TAGATCAAGT | TATTCTCAGT | AAGAATACCT | 1550 |
| CAGAACATGG | ACAACTAGAT | TTATTATACC | CTAGTATTGA | CAGTGAGAGT | 1600 |
| GAAATATTAC | CAGGGGAGAA | TCAAGTCTTT | TATGATAATA | GAACTCAAAA | 1650 |
| TGTTGATTAT | TTGAATTCTT | ATTATTACCT | AGAATCTCAA | AAACTAAGTG | 1700 |
| ATAATGTTGA | AGATTTTACT | TTTACGAGAT | CAATTGAGGA | GGCTTTGGAT | 1750 |

-continued

```
AATAGTGCAA AAGTATATAC TTACTTTCCT ACACTAGCTA ATAAAGTAAA      1800

TGCGGGTGTT CAAGGTGGTT TATTTTTAAT GTGGGCAAAT GATGTAGTTG      1850

AAGATTTTAC TACAAATATT CTAAGAAAAG ATACATTAGA TAAAATATCA      1900

GATGTATCAG CTATTATTCC CTATATAGGA CCCGCATTAA ATATAAGTAA      1950

TTCTGTAAGA AGAGGAAATT TTACTGAAGC ATTTGCAGTT ACTGGTGTAA      2000

CTATTTTATT AGAAGCATTT CCTGAATTTA CAATACCTGC ACTTGGTGCA      2050

TTTGTGATTT ATAGTAAGGT TCAAGAAAGA AACGAGATTA TTAAAACTAT      2100

AGATAATTGT TTAGAACAAA GGATTAAGAG ATGGAAAGAT TCATATGAAT      2150

GGATGATGGG AACGTGGTTA TCCAGGATTA TTACTCAATT TAATAATATA      2200

AGTTATCAAA TGTATGATTC TTTAAATTAT CAGGCAGGTG CAATCAAAGC      2250

TAAAATAGAT TTAGAATATA AAAAATATTC AGGAAGTGAT AAAGAAAATA      2300

TAAAAAGTCA AGTTGAAAAT TTAAAAAATA GTTAGATGT AAAAATTTCG       2350

GAAGCAATGA ATAATATAAA TAAATTTATA CGAGAATGTT CCGTAACATA      2400

TTTATTTAAA AATATGTTAC CTAAAGTAAT TGATGAATTA AATGAGTTTG      2450

ATCGAAATAC TAAAGCAAAA TTAATTAATC TTATAGATAG TCATAATATT      2500

ATTCTAGTTG GTGAAGTAGA TAAATTAAAA GCAAAAGTAA ATAATAGCTT      2550

TCAAAATACA ATACCCTTTA ATATTTTTTC ATATACTAAT AATTCTTTAT      2600

TAAAAGATAT AATTAATGAA TATTTCAATA ATATTAATGA TTCAAAAATT      2650

TTGAGCCTAC AAAACAGAAA AAATACTTTA GTGGATACAT CAGGATATAA      2700

TGCAGAAGTG AGTGAAGAAG GCGATGTTCA GCTTAATCCA ATATTTCCAT      2750

TTGACTTTAA ATTAGGTAGT TCAGGGGAGG ATAGAGGTAA AGTTATAGTA      2800

ACCCAGAATG AAAAATATTGT ATATAATTCT ATGTATGAAA GTTTTAGCAT     2850

TAGTTTTTGG ATTAGAATAA ATAAATGGGT AAGTAATTTA CCTGGATATA      2900

CTATAATTGA TAGTGTTAAA ATAACTCAG GTTGGAGTAT AGGTATTATT       2950

AGTAATTTTT TAGTATTTAC TTTAAAACAA AATGAAGATA GTGAACAAAG      3000

TATAAATTTT AGTTATGATA TATCAAATAA TGCTCCTGGA TACAATAAAT      3050

GGTTTTTTGT AACTGTTACT AACAATATGA TGGGAAATAT GAAGATTTAT      3100

ATAAATGGAA AATTAATAGA TACTATAAAA GTTAAAGAAC TAACTGGAAT      3150

TAATTTTAGC AAAACTATAA CATTTGAAAT AAATAAAATT CCAGATACCG      3200

GTTTGATTAC TTCAGATTCT GATAACATCA ATATGTGGAT AAGAGATTTT      3250

TATATATTTG CTAAAGAATT AGATGGTAAA GATATTAATA TATTATTTAA      3300

TAGCTTGCAA TATACTAATG TTGTAAAAGA TTATTGGGA AATGATTTAA       3350

GATATAATAA AGAATATTAT ATGGTTAATA TAGATTATTT AAATAGATAT      3400

ATGTATGCGA ACTCACGACA AATTGTTTTT AATCACGTA GAAATAATAA       3450

TGACTTCAAT GAAGGATATA AAATTATAAT AAAAAGAATC AGAGGAAATA      3500

CAAATGATAC TAGAGTACGA GGAGGAGATA TTTTATATTT TGATATGACA      3550

ATTAATAACA AAGCATATAA TTTGTTTATG AAGAATGAAA CTATGTATGC      3600

AGATAATCAT AGTACTGAAG ATATATATGC TATAGGTTTA AGAGAACAAA      3650

CAAAGGATAT AAATGATAAT ATTATATTTC AAATACAACC AATGAATAAT      3700

ACTTATTATT ACGCATCTCA AATATTTAAA TCAATTTTTA ATGGAGAAAA      3750
```

| | |
|---|---|
| TATTTCTGGA ATATGTTCAA TAGGTACTTA TCGTTTTAGA CTTGGAGGTG | 3800 |
| ATTGGTATAG ACACAATTAT TTGGTGCCTA CTGTGAAGCA AGGAAATTAT | 3850 |
| GCTTCATTAT TAGAATCAAC ATCAACTCAT TGGGGTTTTG TACCTGTAAG | 3900 |
| TGAATAAATA ATGATTAATA ATATAAATTA TGTTAAATAT TTTAATATTA | 3950 |

(2) INFORMATION FOR SEQ ID NO: 3:

(i) SEQUENCE CHARACTERISTICS:
        (A) LENGTH: 5
        (B) TYPE: AMINO ACID
        (D) TOPOLOGY: LINEAR     (xi) SEQUENCE DESCRIPTION: SEQ ID NO: 3:

His Glu Xaa Xaa His
1          5

(2) INFORMATION FOR SEQ ID NO: 4:

(i) SEQUENCE CHARACTERISTICS:
        (A) LENGTH: 25
        (B) TYPE: NUCLEIC ACID
        (C) STRANDEDNESS: SINGLE
        (D) TOPOLOGY: LINEAR     (iv) ANTI-SENSE: NO     (xi) SEQUENCE DESCRIPTION: SEQ ID NO: 4:

| | |
|---|---|
| CCCAATAACA ATTAACAACT TTAAT | 25 |

(2) INFORMATION FOR SEQ ID NO: 5:

(i) SEQUENCE CHARACTERISTICS:
        (A) LENGTH: 33
        (B) TYPE: NUCLEIC ACID
        (C) STRANDEDNESS: SINGLE
        (D) TOPOLOGY: LINEAR     (iv) ANTI-SENSE: NO     (xi) SEQUENCE DESCRIPTION: SEQ ID NO: 5:

| | |
|---|---|
| TTTGGTACCC ATTAAAATTA GTATTGGATC CAT | 33 |

(2) INFORMATION FOR SEQ ID NO: 6:

(i) SEQUENCE CHARACTERISTICS:
        (A) LENGTH: 39
        (B) TYPE: NUCLEIC ACID
        (C) STRANDEDNESS: SINGLE
        (D) TOPOLOGY: LINEAR     (iv) ANTI-SENSE: NO     (xi) SEQUENCE DESCRIPTION: SEQ ID NO: 6:

| | |
|---|---|
| TTTGGTACCC TTAATAATGC AATGCATAAT TTATATGGA | 39 |

(2) INFORMATION FOR SEQ ID NO: 7:

(i) SEQUENCE CHARACTERISTICS:
        (A) LENGTH: 25
        (B) TYPE: NUCLEIC ACID
        (C) STRANDEDNESS: SINGLE
        (D) TOPOLOGY: LINEAR     (iv) ANTI-SENSE: NO     (xi) SEQUENCE DESCRIPTION: SEQ ID NO: 7:

```
GAATTCAAAT AATCAACATT TTGAG                                                25

(2) INFORMATION FOR SEQ ID NO:8:

(i) SEQUENCE CHARACTERISTICS:
         (A) LENGTH:  27
         (B) TYPE:  NUCLEIC ACID
         (C) STRANDEDNESS:  SINGLE
         (D) TOPOLOGY:  LINEAR (iv) ANTI-SENSE: NO (xi) SEQUENCE DESCRIPTION:  SEQ ID NO: 8:

TTTGAATTCT TATTATTACC TAGAATC                                              27

(2) INFORMATION FOR SEQ ID NO: 9:

(i) SEQUENCE CHARACTERISTICS:
         (A) LENGTH:  32
         (B) TYPE:  NUCLEIC ACID
         (C) STRANDEDNESS:  SINGLE
         (D) TOPOLOGY:  LINEAR (iv) ANTI-SENSE: NO (xi) SEQUENCE DESCRIPTION:  SEQ ID NO: 9:

TTTGAGCTCT TATTCACTTA CAGGTACAAA AC                                        32

(2) INFORMATION FOR SEQ ID NO: 10:

(i) SEQUENCE CHARACTERISTICS:
         (A) LENGTH:  11
         (B) TYPE:  AMINO ACID
         (D) TOPOLOGY:  LINEAR (xi) SEQUENCE DESCRIPTION:  SEQ ID NO: 10:

Arg Gly Ser His His His His His His Gly Ser
1               5                   10

(2) INFORMATION FOR SEQ ID NO: 11:

(i) SEQUENCE CHARACTERISTICS:
         (A) LENGTH:  31
         (B) TYPE:  NUCLEIC ACID
         (C) STRANDEDNESS:  SINGLE
         (D) TOPOLOGY:  LINEAR (iv) ANTI-SENSE: NO (xi) SEQUENCE DESCRIPTION:  SEQ ID NO: 11:

CGGTACCATG CCAATAACAA TTAACAACTT T                                         31

(2) INFORMATION FOR SEQ ID NO: 12:

(i) SEQUENCE CHARACTERISTICS:
         (A) LENGTH:  24
         (B) TYPE:  NUCLEIC ACID
         (C) STRANDEDNESS:  SINGLE
         (D) TOPOLOGY:  LINEAR (iv) ANTI-SENSE: NO (xi) SEQUENCE DESCRIPTION:  SEQ ID NO: 12:

AGCTATAGAT CTATAATAAT CCAA                                                 24

(2) INFORMATION FOR SEQ ID NO: 13:
```

```
     (i) SEQUENCE CHARACTERISTICS:
         (A) LENGTH:  13
         (B) TYPE:  AMINO ACID
         (D) TOPOLOGY:  LINEAR (xi) SEQUENCE DESCRIPTION:  SEQ ID NO: 13:

Arg Gly Ser His His His His His His Gly Ser Gly Thr
1               5                   10
```